(12) United States Patent
Berry

(10) Patent No.: US 6,729,329 B2
(45) Date of Patent: May 4, 2004

(54) SYSTEM FOR REMOVAL OF HALOCARBON GAS FROM WASTE ANESTHETIC GASES

(76) Inventor: James M. Berry, 41 Eastbrooke Dr., Jackson, MS (US) 39216

( * ) Notice: Subject to any disclaimer, the term of this patent is extended or adjusted under 35 U.S.C. 154(b) by 113 days.

(21) Appl. No.: 09/922,831

(22) Filed: Aug. 6, 2001

(65) Prior Publication Data

US 2003/0029449 A1 Feb. 13, 2003

(51) Int. Cl.[7] .............................. A62B 7/10; A62B 7/00; A61M 16/00
(52) U.S. Cl. .............................. 128/204.16; 128/205.12
(58) Field of Search ..................... 128/203.12, 203.16, 128/205.27, 203.18, 203.13, 205.12, 204.15, 204.16, 201.21, 201.25, 910

(56) References Cited

U.S. PATENT DOCUMENTS

| | | | | |
|---|---|---|---|---|
| 3,592,191 A | * | 7/1971 | Jackson | 128/203.28 |
| 3,714,942 A | * | 2/1973 | Fischel et al. | 128/201.21 |
| 4,259,303 A | | 3/1981 | Nakaji et al. | |
| 5,044,363 A | | 9/1991 | Burkhart | |
| 5,205,843 A | * | 4/1993 | Kaschemekat et al. | 95/39 |
| 5,520,169 A | * | 5/1996 | Georgieff et al. | 128/204.16 |
| 5,759,504 A | | 6/1998 | Kanno et al. | |
| 5,928,411 A | | 7/1999 | Falb et al. | |
| 6,030,591 A | * | 2/2000 | Tom et al. | 423/240 S |
| 6,080,226 A | | 6/2000 | Dolan et al. | |
| 6,134,914 A | * | 10/2000 | Eschwey et al. | 62/637 |
| 6,405,539 B1 | * | 6/2002 | Stach et al. | 62/3.4 |

OTHER PUBLICATIONS

Brown AC, Canosa–Mas CE, Parr AD, et al.: Tropospheric lifetimes of halogenated anaesthetics. Nature 1989; 341: 635–637.

Langbein T, Sonntag H, Trapp D, et al.: Volatile anaesthetics and the atmosphere: atmospheric lifetimes and atmospheric effects of halothane, enflurane, isoflurane, desflurane and sevoflurane. Br J Anaesth 1999; 82: 66–73.

McCulloch, A.: Letter to Editor regarding Langbein, et al. 1999 paper. Br J Anaesth 2000; 84 (4): 534–36.

* cited by examiner

*Primary Examiner*—Aaron J. Lewis
(74) *Attorney, Agent, or Firm*—Gary L. Bush; Andrews Kurth LLP

(57) ABSTRACT

A system for removing halocarbon gas components from waste anesthetic gases using the resource of cold oxygen from liquid oxygen which is stored cryogenically at a healthcare facility. The oxygen is warmed while cooling of waste anesthetic gases from anesthetizing locations of a healthcare facility. Two heat exchangers/condensers are provided. In the first, the waste gas is cooled to about 0° C. thereby condensing any water vapor in the waste gas. In the second, the waste gas is further cooled to about −150° C. thereby condensing and liquefying the halocarbon gas components, which are removed to a tank for recycling and/or destruction. The remainder of the waste gases (e.g., nitrogen, oxygen and nitrous oxide) are vented to the atmosphere. The warmed oxygen is piped to the healthcare facility for its normal uses after it has been warmed by the waste anesthetic gases in the two heat exchangers/condensers.

4 Claims, 1 Drawing Sheet

SYSTEM FOR REMOVAL OF HALOCARBON GAS FROM WASTE ANESTHETIC GASES

BACKGROUND OF THE INVENTION

1. Field of the Invention

This invention concerns treatment of waste anesthetic gas. In particular the invention pertains to the removal of halocarbons from waste anesthetic gas of a healthcare facility before the gas is discharged to atmosphere in order to decrease atmospheric pollution.

2. Description of the Prior Art

Anesthesia machines in surgical facilities (both hospital and outpatient) emit significant quantities of waste gases. Currently these gases are "scavenged" and diluted with air in a system of dedicated pipes. However, they are then vented to the atmosphere outside the building. The average composition of the waste gases is estimated to be:

| | |
|---|---|
| Oxygen | 25–30% |
| Nitrogen | 60–65% |
| Nitrous oxide | 5–10% |
| Volatile halocarbon | 0.1–0.5% |

The halocarbons (primarily halogenated methyl ethyl ethers) represent an increasingly significant source of environmental concern, because other halocarbon emission has recently been reduced by legislative and other initiatives. These compounds (similar to refrigerants Freon-12® and others) can contribute to ozone depletion and, to a lesser extent, environmental warming. Currently no regulation of these emissions exists, although it is anticipated that regulation of them will occur in the near future.

Several techniques have been employed to treat waste anesthetic gases. U.S. Pat. No. 4,259,303 describes treating laughing gas with a catalyst. Adsorption of anesthetic gases by charcoal granules is described in U.S. Pat. No. 5,044,363. Destruction of anesthetic gases by heating in the presence of a catalyst is described in U.S. Pat. No. 5,759,504.

Identification of Objects of the Invention

A primary object of the invention is to provide a system and method for removing volatile halocarbons of waste anesthetic gases from a surgical facility before such gases are vented to the atmosphere.

Another object of the invention is to provide an economical system and method for substantially preventing atmospheric venting of volatile halocarbons of waste anesthetic gas while eliminating the need of prior art catalysts, charcoal granules and heating techniques.

SUMMARY OF THE INVENTION

The objects identified above, as well as other advantages and features are embodied in a system and method which uses condensation ("cold trap") technology such that the temperature of the halocarbons is lowered to a point where the vapor pressure of the halocarbons is negligible. In other words, the halocarbon gas is liquefied through refrigeration. The source of refrigeration is liquid oxygen at a surgical facility, which must be warmed for ordinary use at a surgical facility, such as a hospital or outpatient clinic. The waste anesthetic gas is passed first through a first set of condensing coils where water vapor in the gas is condensed by virtue of the cold oxygen flowing through the condensing coils. The remainder of the gas from the first set of condensing coils is passed to a second set of coils (with cold oxygen gas flowing through them) where the gas temperature is lowered to about −150° C. at which point the halocarbons are liquefied. The remainder of the anesthetic gas is vented to atmosphere.

DESCRIPTION OF PREFERRED EMBODIMENTS OF THE INVENTION

Figure 1:
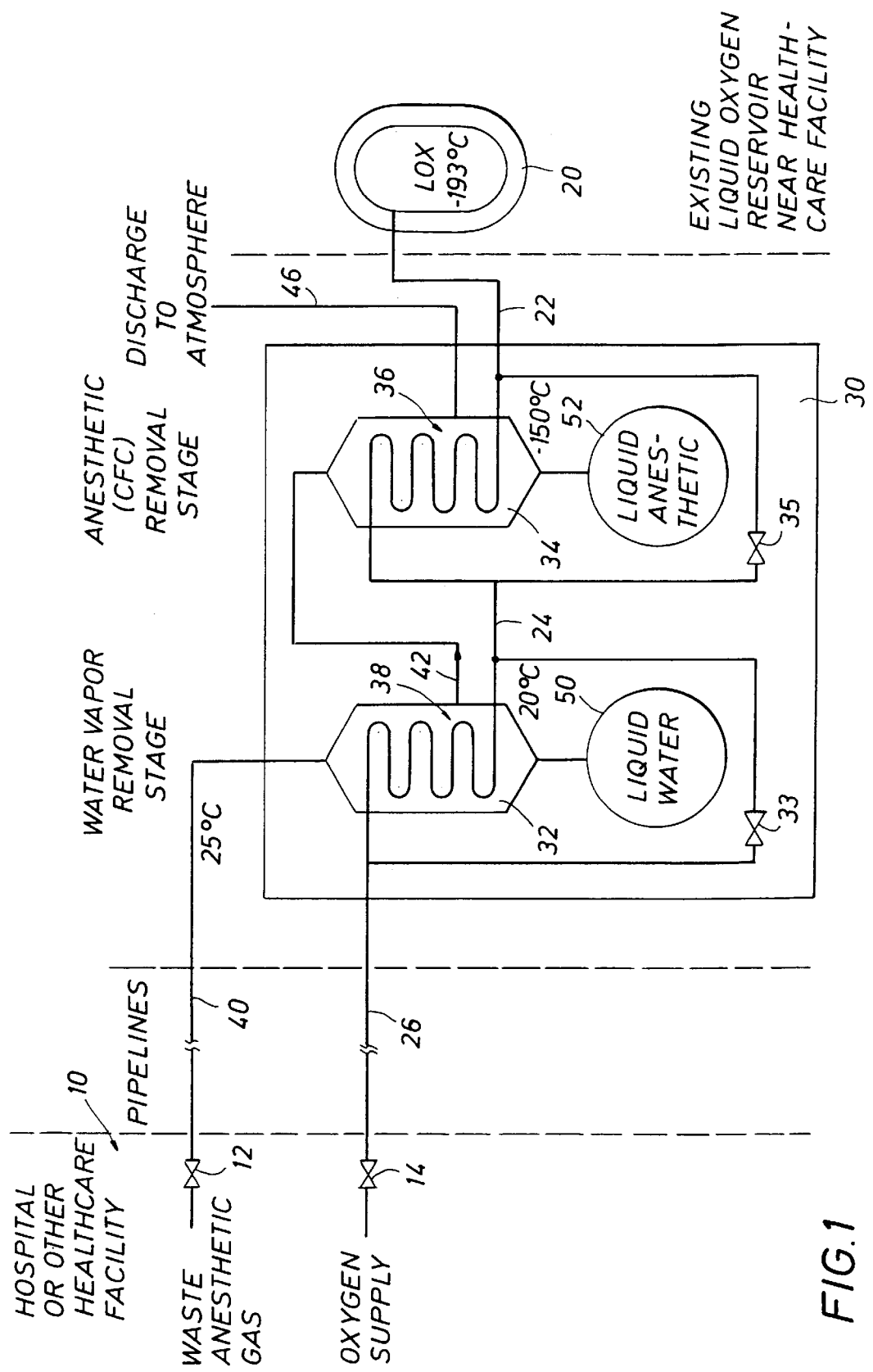
FIG. 1 illustrates in schematic form the process and system by which halocarbon gas components of waste anesthetic gases are liquefied using a source of liquefied oxygen at a surgical facility for removal of such gas components prior to venting of the waste anesthetic gases to the atmosphere.

FIG. 1 illustrates the system according to the invention which includes a surgical facility, or hospital or other healthcare facility 10. Collected waste anesthetic gas may be passed through a valve 12 in facility which may be fluidly connected to flowline 40. A flowline 26 for oxygen supply of the facility 10 may include a valve 14 to which oxygen flowlines inside the hospital may be fluidly connected.

A source of liquid oxygen is schematically illustrated by tank 20 which exists near the healthcare facility. Prior art hospital facilities have passed the liquid oxygen of a tank such as 20 through warming facilities such that the temperature of the liquid oxygen at about −193° C. is warmed to room temperature (about 25° C.) before reaching the facility 10 via flowline 26. In the past, liquid oxygen has been warmed by heat exchangers, exposed to ambient air located near each tank 20. The warmed gas is then applied to flow paths to the point of patient use, e.g. via flowlines connected to valve 14 for example in the healthcare facility 10.

According to the system of the invention as illustrated in FIG. 1, an enclosure 30 is provided which includes first and second condensers 32 and 34. The outlet line 22 for liquid oxygen from tank 20 is fluidly connected to the condensing coils 36 of second tank 34. The outlet of condensing coils 36 is fluidly connected via flowline 24 to the input of coils 38 of first tank 32. The outlet of coils 38 is fluidly connected via flowline 26 to valve 14 and flowlines connected thereto (not shown) of healthcare facility 10.

A flowline 40 from valve 12 which connects to flowlines in the facility 10 (not shown) of the waste anesthetic gas of healthcare facility 10 is applied to an inlet of heat exchanger/condenser 32. The temperature of oxygen flowing at the inlet of the coils 38 is approximately 0° C. or above controlled thermostatically by valve 33, and enters at a temperature of room temperature at oxygen supply valve 14, i.e., about 25° C. The temperature of the waste anesthetic gas enters heat exchanger/condenser 32 via flowline 40 at a temperature of about room temperature. The waste anesthetic gas enters at the top or entrance of heat exchanger/condenser 32 and passes downward through coils 38. Water vapor in the waste anesthetic gas condenses to liquid water at a temperature slightly above 0° C. and falls by gravity to tank 50 for storage and removal.

The cooled gas near the bottom of tank 32 is conducted via flowline 42 to the top or entrance of heat exchanger/condenser 34 where it is applied at a temperature greater than about 0° C. The cooled gas applied to the top of heat exchanger/condenser 34 passes over coils 36 where the temperature of oxygen from flowline 22 enters at about −150° C. and rises to an increased temperature, at the exit to flowline 24. If necessary, an intermediate bypass valve 35 may be provided in line 24 to bring the temperature at the inlet of coils 38 to about 0° C. Thus, the temperature of the waste anesthetic gas from flowline 42 is lowered while passing over the coils 36 such that halocarbons of the waste gas are liquefied and are discharged below into tank 52. The remainder of the waste anesthetic gas, i.e., those components which are not harmful to the atmosphere, are vented to the atmosphere via flowline 46 or subjected to further processing by existing catalytic techniques.

The system described above requires only three additional components to those which already exist at healthcare facilities:

1. piping for the "evacuation" gases to the location of the liquid oxygen storage;
2. a heat exchanger/cold condenser system for installation into the oxygen line and the waste gas line; and
3. trap tanks 50, 52 for holding of water and liquid halocarbon from the heat exchanger/condenser system.

Exhaust gas via flowline 40 from an average hospital is 500–1000 l/min composed of (v/v):

| | |
|---|---|
| Oxygen | 25–30% |
| Nitrogen | 60–65% |
| Nitrous oxide | 5–10% |
| Volatile halocarbon | 0.1–0.5%, at an average temperature of 30° C. with humidity of 40–60%. |

Oxygen inflow, e.g. from line 22, to a hospital averages 1000–2000/min (as gas) at a temperature of approximately −150° C. These two liquid streams, liquid oxygen via line 22 and room temperature waste anesthetic gas via line 40 are passed in a countercurrent heat exchanger arrangement 30 which results in oxygen output at about 25° C. and waste gas at about −150° C. (with halocarbon liquefied and trapped). The high humidity of the waste gas requires a preliminary removal of water vapor by means of a water condenser 32 operating near 0° C. If water vapor in the waste gas is not removed, it will freeze and impair the function of the anesthetic condenser 34.

Advantages of the Invention

Existing oxygen storage and delivery systems of healthcare facilities will see minimal impact where the system of FIG. 1 is installed. The exchanger arrangement 30 should be installed (FIG. 1) as close as possible to the liquid oxygen storage unit 20, replacing existing heat exchangers, to maximize the cooling of waste gases. Further warming of oxygen supplies is achieved by the first stage condenser 32.

Additional piping for waste gas delivery to the device can be designed for relatively low pressures, although oxygen content of this stream could be as high as 40–50%. Such a high percentage of oxygen in the waste gas flow line 40 requires oxygen-clean installation precautions.

The system of FIG. 1 advantageously:

1. reduces anesthetic-related halocarbon emissions from a healthcare facility into the atmosphere by about 99%;
2. requires minimal additional investment for a healthcare facility with only small ongoing costs; and
3. provides the possibility of redistilling and reusing a large fraction of the anesthetic halocarbon used in the facility and recovered in tank 52.

The method used by the system of FIG. 1 uses the resource common to almost all healthcare facilities: liquid oxygen stored cryogenically in insulated tanks 20. The liquid oxygen must be warmed from about −190° C. to near room temperature for patient use at tank 14 in healthcare facility 10. This is currently done by heat exchangers, exposed to ambient air, located near each tank. The warmed gas is then piped to point of patient use.

This potent source of cold of liquid oxygen at a healthcare facility is more efficiently used by combining the warming of oxygen via flowlines 22, 24, 26 with the cooling of waste gases via flowlines 40, 42, 46 from anesthetizing locations in facility 10 in countercurrent heat exchangers 32, 34 using a two-step process. The first step in heat exchanger/condenser 32 cools the waste gas to near 0° C. while condensing any water vapor. The second step cools the gas in heat exchanger/condenser 34 to −150° C. while condensing and liquefying the halocarbon, which is then captured in tank 52 and recycled, if desired. The remainder of waste gases (mostly nitrogen, oxygen and nitrous oxide) are exhausted to the atmosphere via line 46 (or further processed by existing catalytic technology).

What is claimed is:

1. In a healthcare facility including a first flowline fluidly connected to a source of waste anesthetic gases and extending therefrom to the atmosphere and a source (20) of liquefied gas with a second flowline extending from said source of liquefied gas to a gas supply outlet (14) in the facility, the improvement comprising, a heat exchanger (30) conductively coupled between said first flowline and said second flowline whereby halocarbon gas components of said waste anesthetic gases are liquefied and prevented from flowing to said atmosphere and said gas from said source of liquefied gas is warmed by the exchange of heat between said waste anesthetic gases and said gas from said liquefied source of gas, said liquefied gas source including liquefied oxygen, said heat exchanger (30) including a first heat exchanger/condenser (32) and a second heat exchanger/condenser (34) wherein, said first flowline is fluidly coupled to said first heat exchanger/condenser (32) for cooling said waste anesthetic gas for liquefying water vapor of said anesthetic gas from said first flowline and is fluidly coupled to said second heat exchanger/condenser (34) for liquefying said halocarbon gas components, and said second flowline is fluidly coupled to coils (36) of said second heat exchanger/condenser (34) where heat is exchanged between gas from said source of liquefied gas and said waste anesthetic gas and is fluidly coupled to coils (38) of said first heat exchanger/condenser (32) where additional heat is exchanged between said waste anesthetic gas and said gas from said liquefied gas source.

2. A system for preventing venting to the atmosphere of halocarbon gas components of waste anesthetic gases from a healthcare facility comprising, a source (20) of liquid oxygen, an outlet (12) of waste anesthetic gases located inside said facility, an outlet (14) of gaseous oxygen located inside said facility, an atmospheric vent line (46), a first heat exchanger/condenser (32) having an inlet fluidly coupled to said outlet (12) of waste anesthetic gases and an outlet, said first heat exchanger/condenser (32) also having a first cooling coil (38) positioned therein with an outlet of said first cooling coil (38) fluidly coupled to said outlet (14) of gaseous oxygen, said first cooling coil (38) having an inlet, a second heat exchanger/condenser (34) having an inlet which is fluidly coupled to said outlet of said first heat exchanger/condenser (32) and an outlet which is fluidly coupled to said atmospheric vent line (46), said second heat exchanger/condenser (34) also having a second cooling coil (36) positioned therein with an outlet of said second cooling coil (36) fluidly coupled to said inlet of said first cooling coil (38) and an inlet of said second cooling coil fluidly coupled to said source (20) of liquid oxygen, first heat exchanger/condenser (32) having a first tank (50) for collecting water which is liquefied from water in said waste anesthetic gases within said first heat exchanger/condenser (32), and said second heat exchanger/condenser (34) having a second tank (52) for collecting liquefied halocarbons from waste anesthetic gases within said second heat exchanger/condenser (34).

3. The system of claim 2 wherein, said waste anesthetic gas enters said first heat exchanger/condenser (32) at room temperature and exits at about 0° C., and said waste anesthetic gas enters said second exchanger/condenser (34) at about 0° C. and exits at a temperature below which halocarbon gas is liquefied.

4. The system of claim 3, wherein, oxygen from said source of liquefied oxygen enters said coil (36) of said second exchanger/condenser (34) at a temperature of about −150° C. and enters at a temperature of about 0° C. into said coil (38) of said first heat exchanger/condenser (38) and exits therefrom for supply to said healthcare facility.

* * * * *

UNITED STATES PATENT AND TRADEMARK OFFICE
CERTIFICATE OF CORRECTION

PATENT NO. : 6,729,329 B2 Page 1 of 1
DATED : May 4, 2004
INVENTOR(S) : James M. Berry It is certified that error appears in the above-identified patent and that said Letters Patent is hereby corrected as shown below:

Column 3,
Line 31, delete "1000-2000/min", insert -- 1000-2000 1/min --

Signed and Sealed this

Seventh Day of September, 2004

JON W. DUDAS
*Acting Director of the United States Patent and Trademark Office*